United States Patent [19]

Sih

[11] Patent Number: 4,474,966

[45] Date of Patent: Oct. 2, 1984

[54] 19-HYDROXY-7A-HOMO-PGI$_1$ AND 19-HYDROXY-19-METHYL-7A-HOMO-PGI$_1$ COMPOUNDS

[75] Inventor: John C. Sih, Kalamazoo, Mich.

[73] Assignee: The Upjohn Company, Kalamazoo, Mich.

[21] Appl. No.: 336,197

[22] Filed: Dec. 31, 1981

Related U.S. Application Data

[60] Continuation-in-part of Ser. No. 126,512, Mar. 3, 1980, Pat. No. 4,328,156, which is a division of Ser. No. 054,720, Jul. 5, 1979, Pat. No. 4,225,507.

[51] Int. Cl.$^3$ .............................................. C07D 311/02
[52] U.S. Cl. .................................... 548/252; 549/396; 548/253
[58] Field of Search ...................... 260/345.2; 548/252, 548/253; 549/396

[56] References Cited

U.S. PATENT DOCUMENTS 4,123,441 10/1978 Johnson et al. .................. 260/345.2
4,230,721 10/1980 Gandolfi et al. ................. 260/345.2

*Primary Examiner*—Nicky Chan
*Attorney, Agent, or Firm*—L. Ruth Hattan

[57] ABSTRACT

The present invention provides novel 19-hydroxy-7a-homo-PGI$_1$ 19-hydroxy-19-methyl-7a-homo-PGI$_1$ compounds which are useful for pharmacological purposes, e.g., anti-asthmatic indications.

3 Claims, No Drawings

19-HYDROXY-7A-HOMO-PGI$_1$ AND 19-HYDROXY-19-METHYL-7A-HOMO-PGI$_1$ COMPOUNDS

DESCRIPTION

Cross Reference To Related Application

The present invention is a continuation-in-part application of U.S. Ser. No. 126,512, filed Mar. 3, 1980 now U.S. Pat. No. 4,328,156, issued May 4, 1982, which is a division of Ser. No. 054,720, filed July 5, 1979, issued Sept. 30, 1980 as U.S. Pat. No. 4,225,507.

BACKGROUND OF THE INVENTION

The present invention provides novel prostacyclin analogs. Particularly, the present invention relates to prostacyclin in analogs substituted at the C-19 position by hydroxy.

Particularly, the present invention relates to 19-hydroxy-7a-homo-PGI$_1$ and 19-hydroxy-19-methyl-7a-homo-PGI$_1$ compounds. The novel prostacyclin analogs are useful for pharmacological purposes, e.g., as anti-asthmatic agents. The preparation and use of these compounds is incorporated herein by reference from U.S. Pat. Nos. 4,225,507 and 4,225,508, each issued Sept. 30, 1980.

PRIOR ART

For background on prostacyclin, see for example R. A. Johnson, et al., Prostaglandins 12, 915–928 (1976) and R. A. Johnson, et al, J. Am. Chem. Soc. 100, 7690–7704 (1978), and, as to pharmacological activity, the references cited therein. For analogs of prostacyclin, see, for example, J. Fried, et al, Proc. Natl. Acad. Sci. U.S.A. 74, 2199–2203, K. C. Nicolaou, et al, J.C.S. Chem. Comm. 1977, 331–332, N. A. Nelson, J. Am. Chem. Soc. 99, 7362–7363 (1977), and K. Kojima, et al, Tet. Lette., 1978, (1977), and K. Kojima, et al, Tet. Lett., 1978, 3743–3746. Regarding the nomenclature for analogs of PGI$_2$, see R. A. Johnson, et al, Prostaglandins 15, 737–740 (1978).

SUMMARY OF THE INVENTION

The present invention particularly provides a prostacyclin-type compound of the formula

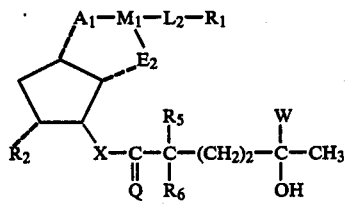

wherein W is H or —CH$_3$;
wherein A$_1$ is —O— (oxa) and E$_2$ is —CH$_2$CH$_2$—;
wherein L$_2$ is —(CH$_2$)$_j$—, wherein j is one to 4, inclusive;
wherein M$_1$ is

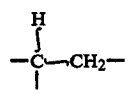

wherein Q is oxo, α—H:β—H, α—OH:β—R$_4$, or α—R$_4$:β—OH,
wherein R$_4$ is hydrogen or alkyl of one to 4 carbon atoms, inclusive,
wherein R$_1$ is
 (1) —COOR$_3$,
 (2) —CH$_2$OH,
 (3) —CH$_2$N(R$_7$)(R$_8$),
 (4) —CO—N(R$_7$)(R$_8$),
 (5) —CO—NH—SO$_2$—R$_{15}$, or
 (6) tetrazolyl,
wherein R$_3$ is
 (a) hydrogen,
 (b) alkyl of one to 12 carbon atoms, inclusive,
 (c) cycloalkyl of 3 to 10 carbon atoms, inclusive,
 (d) aralkyl of 7 to 12 carbon atoms, inclusive,
 (e) phenyl,
 (f) phenyl substituted with one, 2, or 3 chloro or alkyl groups of one to 3 carbon atoms, inclusive;
 (g) —(Ph)—CO—CH$_3$,
 (h) —(p—Ph)—NH—CO—(p—Ph)—NH—CO—CH$_3$,
 (i) —(p—Ph)—NH—CO—(p—Ph),
 (j) —(p—Ph)—NH—CO—CH$_3$,
 (k) —(p—Ph)—NH—CO—NH$_2$,
 (l) —(p—Ph)—CH=N—NH—CO—NH$_2$,
 (m) β-naphthyl,
 (n) —CH$_2$—CO—R$_{16}$,
wherein —(Ph)— is inter-phenylene and —(p—Ph) is inter-para-phenylene or para-phenyl;
wherein R$_{16}$ is phenyl, p-bromophenyl, p-biphenylyl, p-nitrophenyl, p-benzamidophenyl, or 2-naphthyl, or
 (o) a pharmacologically acceptable cation; wherein R$_7$ and R$_8$ are hydrogen, alkyl of one to 12 carbon atoms, inclusive, benzyl, or phenyl, being the same or different, and wherein R$_{15}$ is hydrogen, alkyl of one to 12 carbon atoms, inclusive, phenyl, phenyl-substituted with one, 2, or 3 chloro or alkyl groups of one to 3 carbon atoms, inclusive, or phenyl substituted with hydroxycarbonyl or alkoxycarbonyl of one to 4 carbon atoms, inclusive,
wherein R$_2$ is hydrogen, hydroxyl, or hydroxymethyl,
wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro, and
wherein X is
 (1) trans—CH=CH—,
 (2) cis—CH=CH—,
 (3) —C≡C—, or
 (4) —CH$_2$CH$_2$—.
with the further proviso that when R$_1$ is —COOR$_3$ wherein R$_3$ is hydrogen or alkyl of one to 12 carbon atoms, inclusive; —CH$_2$OH; —CON(R$_7$)(R$_8$); or tetrazolyl; one of R$_5$ or R$_6$ is other than hydrogen.

I claim:
1. A prostacyclin-type compound of the formula

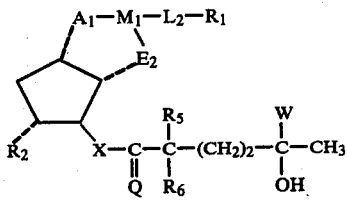

wherein W is H or CH₃;
wherein A₁ is —O— (oxa) and E₂ is —CH₂CH₂—;
wherein L₂ is —(CH₂)ⱼ—, wherein j is one to 4, inclusive;
wherein M₁ is

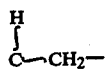

wherein Q is oxo, α—H:β—H, α—OH:β—R₄, or α—R₄:β—OH,
  wherein R₄ is hydrogen or alkyl of one to 4 carbon atoms, inclusive,
wherein R₁ is
  (1) —COOR₃,
  (2) —CH₂OH,
  (3) —CH₂N(R₇)(R₈),
  (4) —CO—N(R₇)(R₈),
  (5) —CO—NH—SO₂—R₁₅, or
  (6) tetrazolyl,
wherein R₃ is
  (a) hydrogen,
  (b) alkyl of one to 12 carbon atoms, inclusive,
  (c) cycloalkyl of 3 to 10 carbon atoms, inclusive,
  (d) aralkyl of 7 to 12 carbon atoms, inclusive,
  (e) phenyl,
  (f) phenyl substituted with one, 2, or 3 chloro or alkyl groups of one to 3 carbon atoms, inclusive;
  (g) —(Ph)—CO—CH₃,
  (h) —(p—Ph)—NH—CO—(p—Ph)—NH—CO—CH₃,
  (i) —(p—Ph)—NH—CO—(p—Ph),
  (j) —(p—Ph)—NH—CO—CH₃,
  (k) —(p—Ph)—NH—CO—NH₂,
  (l) —(p—Ph)—CH=N—NH—CO—NH₂,
  (m) β-naphthyl,
  (n) —CH₂—CO—R₁₆,
wherein —(Ph)— is inter-phenylene and —(p—Ph) is inter-para-phenylene or para-phenyl;
wherein R₁₆ is phenyl, p-bromophenyl, p-biphenylyl, p-nitrophenyl, p-benzamidophenyl, or 2-naphthyl, or
  (o) a pharmacologically acceptable cation; wherein R₇ and R₈ are hydrogen, alkyl of one to 12 carbon atoms, inclusive, benzyl, or phenyl, being the same or different, and wherein R₁₅ is hydrogen, alkyl of one to 12 carbon atoms, inclusive, phenyl, phenyl-substituted with one, 2, or 3 chloro or alkyl groups of one to 3 carbon atoms, inclusive, or phenyl substituted with hydroxycarbonyl or alkoxycarbonyl of one to 4 carbon atoms, inclusive,
wherein R₂ is hydrogen, hydroxyl, or hydroxymethyl,
wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro, and
wherein X is
  (1) trans—CH=CH—,
  (2) cis—CH=CH—,
  (3) —C≡C—, or
  (4) —CH₂CH₂—,
with the further proviso that when R₁ is —COOR₃ wherein R₃ is hydrogen or alkyl of one to 12 carbon atoms, inclusive; —CH₂OH; —CON(R₇)(R₈); or tetrazolyl; one of R₅ or R₆ is other than hydrogen.

2. A compound of claim 1, wherein W is H.
3. A compound of claim 1, wherein W is —CH₃.

* * * * *